United States Patent
Kim et al.

(10) Patent No.: US 11,987,849 B2
(45) Date of Patent: May 21, 2024

(54) COMPOSITION FOR DETECTING LEPTOSPIROSIS AND METHOD OF DIAGNOSING LEPTOSPIROSIS USING SAME

(71) Applicant: INDUSTRY-ACADEMIC COOPERATION FOUNDATION, CHOSUN UNIVERSITY, Gwangju (KR)

(72) Inventors: Dong Min Kim, Gwangju (KR); You Mi Lee, Gwangju (KR); Choon Mee Kim, Gwangju (KR)

(73) Assignee: Industry-Academic Cooperation Foundation, Chosun University, Gwangju (KR)

( * ) Notice: Subject to any disclaimer, the term of this patent is extended or adjusted under 35 U.S.C. 154(b) by 40 days.

(21) Appl. No.: 17/454,980

(22) Filed: Nov. 15, 2021

(65) Prior Publication Data
US 2022/0154251 A1 May 19, 2022

(30) Foreign Application Priority Data
Nov. 16, 2020 (KR) .......... 10-2020-0153046

(51) Int. Cl.
C12Q 1/68 (2018.01)
C12Q 1/686 (2018.01)
C12Q 1/689 (2018.01)

(52) U.S. Cl.
CPC ........... *C12Q 1/689* (2013.01); *C12Q 1/686* (2013.01); *C12Q 2600/112* (2013.01)

(58) Field of Classification Search
CPC ... C12Q 1/686; C12Q 1/689; C12Q 2600/112
See application file for complete search history.

(56) References Cited

U.S. PATENT DOCUMENTS

| | | | | |
|---|---|---|---|---|
| 2003/0050470 A1* | 3/2003 | An | ............... | C07H 21/00 435/6.14 |
| 2004/0023207 A1* | 2/2004 | Polansky | ............. | A61K 48/005 435/456 |
| 2022/0154251 A1* | 5/2022 | Kim | ............... | C12Q 1/686 |

FOREIGN PATENT DOCUMENTS

| CN | 109852715 A | 6/2019 |
|---|---|---|
| CN | 110218803 A | 9/2019 |
| KR | 10-0868560 B1 | 11/2008 |

OTHER PUBLICATIONS

Cameron et al., 2008. Detection of pathogenic Leptospira bacteria in pinniped populations via PCR and identification of a source of transmission for zoonotic leptospirosis in the marine environment. Journal of Clinical Microbiology, 46(5), pp. 1728-1733. (Year: 2008).*
Cosate et al., 2017. Molecular typing of Leptospira interrogans serovar Hardjo isolates from leptospirosis outbreaks in Brazilian livestock. BMC veterinary research, 13(1), pp. 1-12. (Year: 2017).*
Genbank Accession No. CP006723—Leptospira interrogans serovar Linhai str. 56609 chromosome 1, complete sequence (submitted Sep. 9, 2013, retrieved on Mar. 20, 2023 from http://www.ncbi.nlm.nih.gov/nuccore/CP006723). (Year: 2013).*
Genbank Accession No. DQ208197—Leptospira interrogans insertion sequence IS1500D ORFAB (orfAB) and ORFA (orfA) genes, complete cds (submitted Sep. 16, 2005, retrieved on Mar. 20, 2023 from http://www.ncbi.nlm.nih.gov/nuccore/DQ208197). (Year: 2005).*
Reitstetter, 2006. Development of species-specific PCR primer sets for the detection of Leptospira. FEMS microbiology letters, 264(1), pp. 31-39. (Year: 2006).*
SantaLucia Jr, John. Physical principles and visual-OMP software for optimal PCR design. PCR Primer Design. Humana Press, 2007: pp. 3-33. (Year: 2007).*
Zuerner et al., 1997. Differentiation of Leptospira interrogans isolates by IS1500 hybridization and PCR assays. Journal of clinical microbiology, 35(10), pp. 2612-2617. (Year: 1997).*
Bourhy et al., 2011. Comparison of real-time PCR assays for detection of pathogenic Leptospira spp. in blood and identification of variations in target sequences. Journal of clinical microbiology, 49(6), pp. 2154-2160. (Year: 2011).*
Cosate, M.R.V. et al. "Molecular typing of Leptospira interrogans serovar Hardjo isolates from leptospirosis outbreaks in Brazilian livestock," BMC Vet Res 13, 177 (2017), https://doi.org/10.1186/s12917-017-1081-9 (Jun. 15, 2017).
"Leptospira Interrogans Serovar Linhai Str. 56609 Chromosome 1, Complet—Nucleotide—NCBI." National Center for Biotechnology Information, U.S. National Library of Medicine, https://www.ncbi.nlm.nih.gov/nuccore/CP006723. (Downloaded on Oct. 11, 2021).
Office Action in Korean Application No. 10-2020-0153046 dated Dec. 23, 2021 in 5 pages.
Extended European Search Report for EP Application No. 201208319.0 dated Apr. 11, 2022 in 6 pages.
Notice of Allowance in Korean Application No. 10-2020-0153046 dated Jun. 28, 2022 in 4 pages.

(Continued)

*Primary Examiner* — Stephanie K Mummert
*Assistant Examiner* — Olayinka A Oyeyemi
(74) *Attorney, Agent, or Firm* — Knobbe Martens Olson & Bear LLP

(57) ABSTRACT

This application relates to a composition for diagnosis of leptospirosis and a method for diagnosis of leptospirosis by real-time PCR. For example, the application relates to a pair of primers of SEQ ID NOS: 1 and 2 and a probe of SEQ ID NO: 3, a kit for diagnosis of leptospirosis, comprising the diagnostic composition, and a method for providing information for diagnosis of leptospirosis are provided. The composition and the method can specifically detect *L. interrogans* IS 1500 gene and exhibit excellent accuracy and sensitivity, compared to conventional well-known detection methods. Thus, the simple method through real-time PCR using the composition allows the quick and accurate diagnosis of leptospirosis.

8 Claims, 11 Drawing Sheets

Specification includes a Sequence Listing.

(56) References Cited

OTHER PUBLICATIONS

Smythe, Lee D., et al. "A quantitative PCR (TaqMan) assay for pathogenic Leptospira spp." BMC infectious diseases 2.1 (2002): 1-7.

Zuerner, Richard L., and Carole A. Bolin. "Differentiation of Leptospira interrogans isolates by IS1500 hybridization and PCR assays." Journal of clinical microbiology 35.10 (1997): 2612-2617.

Zuerner, Richard L., David Alt, and Carole A. Bolin. "IS1533-based PCR assay for identification of Leptospira interrogans sensu lato serovars." Journal of Clinical Microbiology 33.12 (1995): 3284-3289.

* cited by examiner

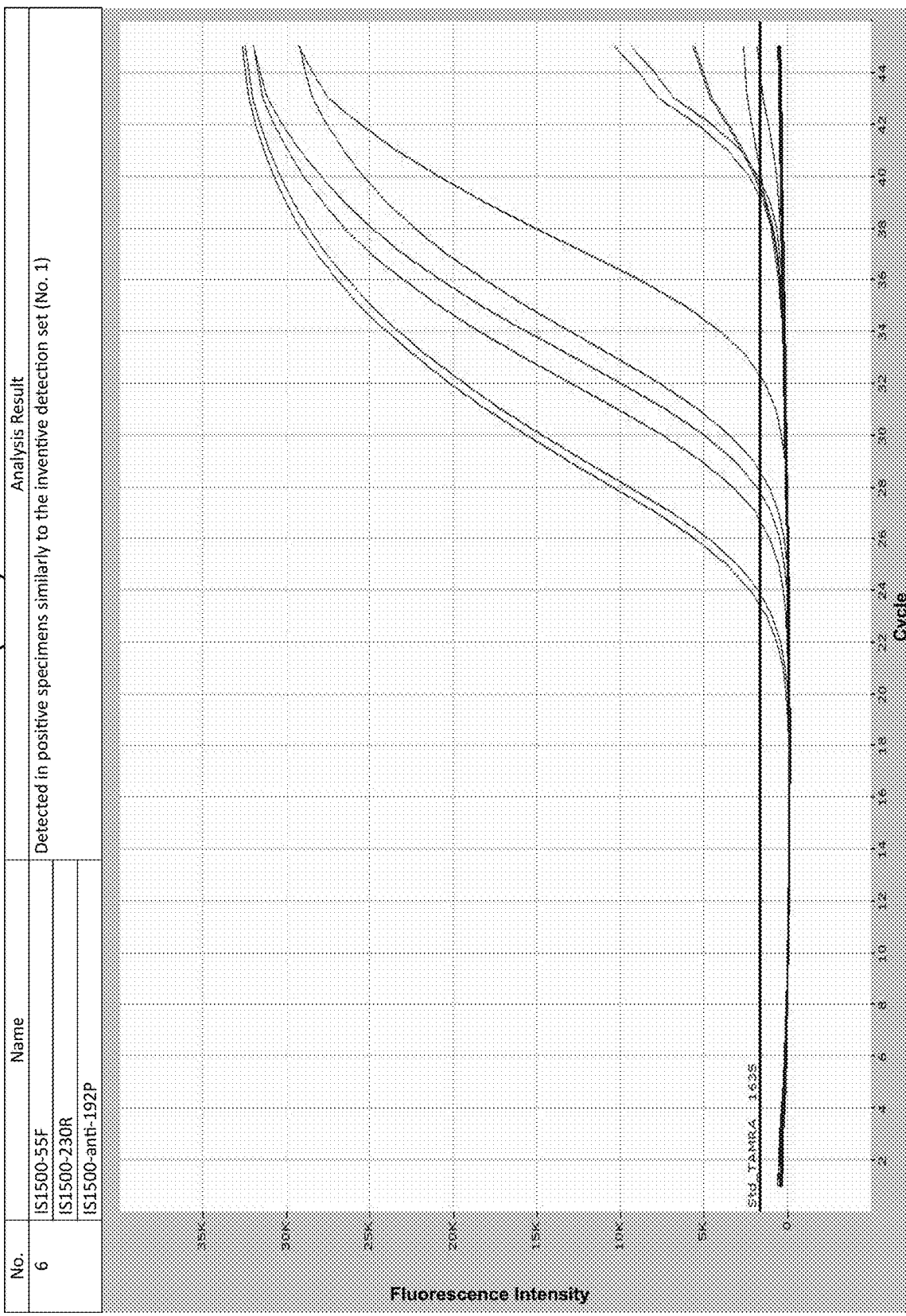

COMPOSITION FOR DETECTING LEPTOSPIROSIS AND METHOD OF DIAGNOSING LEPTOSPIROSIS USING SAME

CROSS-REFERENCE TO RELATED APPLICATION

The present application claims priority to Korean Patent Application No. 10-2020-0153046 filed on Nov. 16, 2020 in the Korean Intellectual Property Office, which is incorporated herein in its entirety by reference.

REFERENCE TO SEQUENCE LISTING

The present application is being filed along with a Sequence Listing in electronic format. The Sequence Listing is provided as a file entitled NAM013002AUS_SeqListing.TXT, which was created and last modified on Nov. 15, 2021, and which is 7,134 bytes in size. The information in the electronic Sequence Listing is hereby incorporated by reference in its entirety.

BACKGROUND

Technical Field

The present disclosure relates to a composition for detecting Leptospirosis and a method for diagnosing Leptospirosis, using real-time PCR.

DESCRIPTION OF RELATED TECHNOLOGY

Leptospirosis, an anthropozoonosis caused by spiral-shaped bacteria of the genus *Leptospira*, was originally recognized as an infectious disease in 1887 as Weil's disease, an acute febrile illness characterized by jaundice and renal failure.

In 1918, a causative bacterium was first isolated from patients with Weil's disease and named *Spirochaeta icterohaemorrhagiae* and then renamed *Leptospira icterohaemorrhagiae*.

As causative pathogens of leptospirosis, 10 bacteria were identified: *Leptospira interrogans, L. alstoni, L. kirschneri, L. noguchii, L. alexane ri, L. welii, L. borgpetersenii, L. santarosai, L. kmetyi*, and *L. mayottensia*.

*L. interrogans* and *L. biflexa* are two species of the genus *Leptospira*, which belongs to the order *Spirochaetales*. *L. interrogans* has about 240 pathogenic serovars divided into 23 serogroups, with serovars *lai, yeonchon, hongchon*, and *canicola* being discovered in Korea.

Wild and domestic animals, such as rodents, cattle, pigs, and dogs, remain chronic carriers after being infected with a contagious source, excreting *leptospira* bacteria in their urine, polluting soil, groundwater, streams, rice paddies, and rivers.

Humans and animals become infected when they are exposed to contaminated urine, water, or surroundings, either directly or indirectly. Farmers, miners, sewage workers, fishers, soldiers, and occupational workers who have a lot of contact with animals are among the high-risk group, and leptospirosis is most common in adult men who are at high risk of exposure owing to occupation, activity, or other factors. It is well known that widespread outbreaks can occur when rice stalks lift up after a strong downpour or when rice is cut during the harvest season.

The signs and symptoms of Weil's disease range from none to mild to severe.

There are many cases of asymptomatic infection. Mild patients without jaundice account for up to 90% of clinically evident infection cases, with severe patients (Weil's disease) accounting for 5-10%. In addition, leptospirosis has been reported to occur in Europe, the Americas, Australia, Vietnam, Thailand, Malaysia, Taiwan, China, and Japan. For Korea, leptospirosis cases were serologically proven in 1942 and since then, there were no reports of human infection. *Leptospira* was first isolated from pulmonary hemorrhage patients in 1984, confirming the presence of the disease in Korea. Since then, leptospiral has been designated, along with scrub typhus, hemorrhagic fever with renal syndrome, and murine typhus, as a third-tier legal communicable disease, in Korea.

SUMMARY

Therefore, an aspect of the present disclosure is to provide a composition for detecting a *leptospira* bacterium, the composition comprising a pair of primers of SEQ ID NOS: 1 and 2; and a probe of SEQ ID NO: 3.

Another aspect of the present disclosure is to provide a diagnostic kit for leptospirosis detection, comprising the composition.

Another aspect of the present disclosure is to develop a method for providing information for diagnosis of leptospirosis.

According to an aspect thereof, the present disclosure provides a composition for detecting a *leptospira* bacterium, the composition comprising a pair of primers of SEQ ID NOS: 1 and 2; and a probe of SEQ ID NO: 3.

In an embodiment of the present disclosure, the *leptospira* bacterium may be *Leptospira interrogans* (*L. interrogans*).

In an embodiment of the present disclosure, a pair of the primers of SEQ ID NOS: 1 and 2 and the probe of SEQ ID NO: 3 may bind specifically to a *L. interrogans* IS 1500 gene including the nucleotide sequence of SEQ ID NO: 22.

In addition, the present disclosure provides a kit for diagnosis of leptospirosis, the kit comprising the composition for detecting a *leptospira* bacterium of the present disclosure.

Furthermore, the present disclosure provides a method for providing information for diagnosis of leptospirosis, the method comprising the steps of: (1) isolating nucleic acid from a specimen separated from a subject suspected of leptospirosis; (2) conducting PCR amplification with the kit of claim 3 with the isolated nucleic acid serving as a template; and (3) identifying *L. interrogans* IS 1500 gene through step (2).

In an embodiment of the present disclosure, the specimen in step (1) may be blood, a tissue, a cell, serum, plasma, saliva, sputum, or urine.

In an embodiment of the present disclosure, the *L. interrogans* IS 1500 gene may include the nucleotide sequence of SEQ ID NO: 22.

In an embodiment of the present disclosure, the PCR amplification may be selected from the group consisting of conventional polymerase chain reaction (C-PCR), nested PCR (N-PCR), multiplex PCR, real-time PCR, quantitative real-time PCR, and reverse transcription PCR.

Being capable of specifically detecting a *L. interrogans* IS 1500 gene with greater accuracy and sensitivity than conventional detection methods, the composition for detecting a *leptospira* bacterium and the method for diagnosis of leptospirosis using the same according to the present disclosure exhibit the effect of diagnosing leptospirosis quickly and accurately in a simple manner using real-time PCR.

BRIEF DESCRIPTION OF THE DRAWINGS

The above and other aspects, features and advantages of the present disclosure will be more apparent from the following detailed description taken in conjunction with the accompanying drawings.

DETAILED DESCRIPTION

Figure 1A:
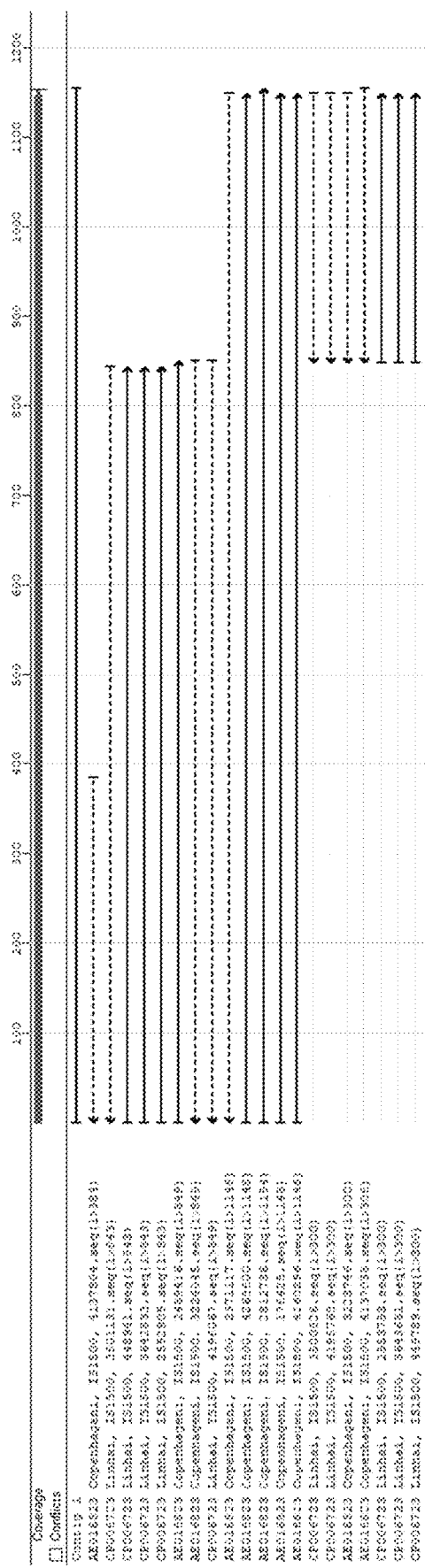
FIG. 1 shows assembly (A) and alignment (B) results of IS1500 genes present in various serovars of *L. interrogans*.
Figure 1B:
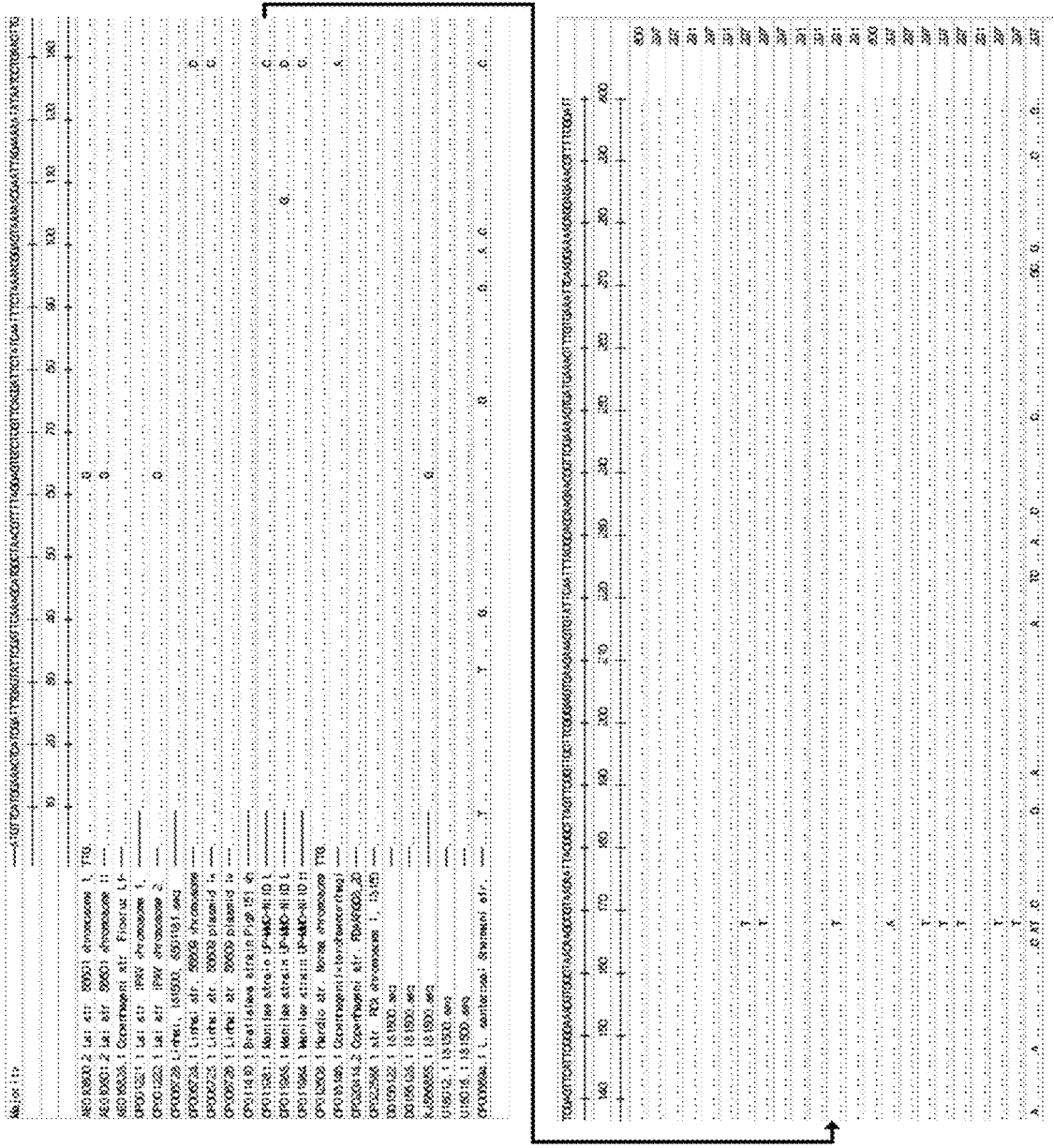
Figure 1B:
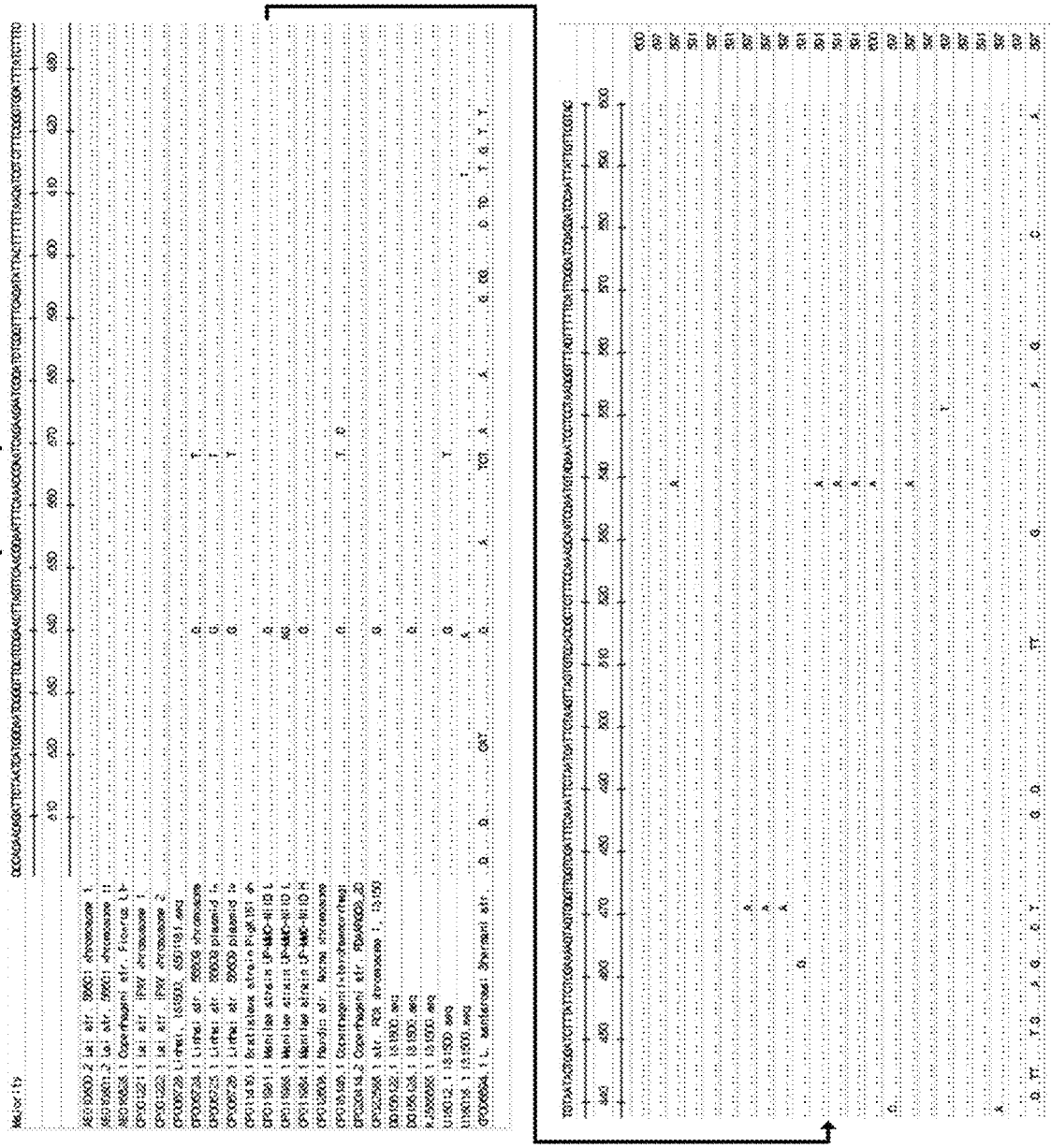
Figure 1B:
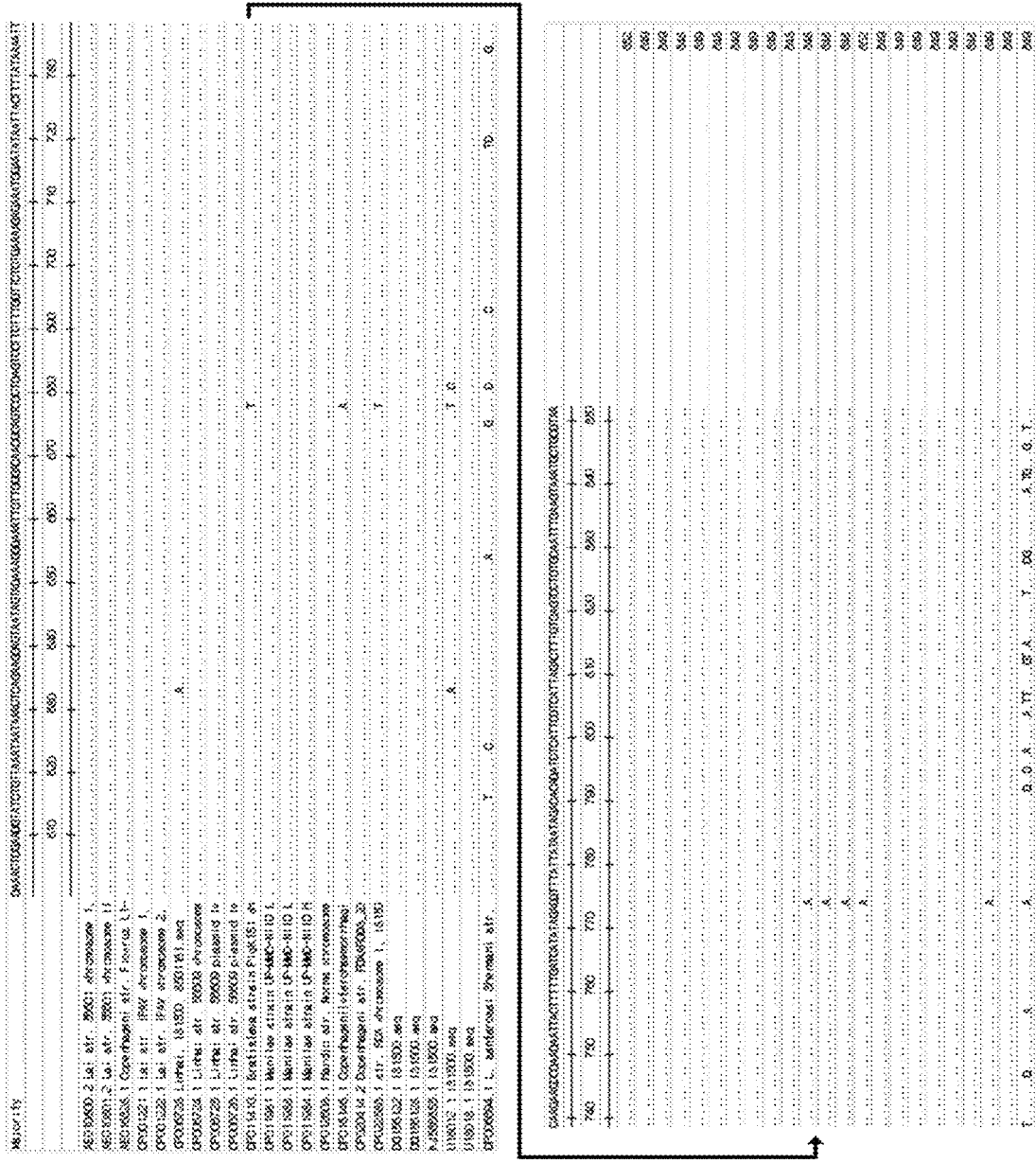

To diagnose leptospirosis, presently, a fourfold or more increase in titer between acute and convalescent specimens validates the diagnosis of leptospirosis.

Alternatively, a microscopic agglutination test is conducted to examine whether a single titer exceeds 1:800. In serological tests, positive results are defined as a four-fold or greater rise in titer of two sera taken in the acute phase and in the convalescent phase with an interval of two weeks or longer therebetween as measured by passive hemagglutination or microscopic agglutination test (MAT), or diagnostic estimation may be made of leptospirosis when a titer of 1:200 or greater is detected as measured by MAT.

However, the currently used detection methods have a difficulty in early diagnosis because a rise in titer starts one to two weeks after onset of the symptoms. Rapid and accurate diagnosis of leptospirosis cannot be expected from the conventional methods.

Therefore, there is an urgent need for development of a novel method capable of diagnosing leptospirosis in a quick, accurate, and convenient manner.

The present disclosure is defined by the provision of a novel composition for detecting a *leptospira* bacteria, allowing for the rapid and accurate diagnosis of leptospirosis.

The current inventors conducted extensive research into a method for accurately and quickly detecting a *leptospira* bacterium in order to accurately and quickly diagnose and treat the infection of *leptospira* causative of the onset of leptospirosis.

Inventors discovered that a *leptospira* insertion sequence (IS) 1500 gene, which exists in multiple copies in *leptospira*, can be used as a novel target marker for detecting a *leptospira* to develop primers and a probe that bind exclusively to the isolated IS (insertion sequence) 1500 gene, allowing for excellent sensitivity and accuracy in diagnosing *leptospira* bacterium infection.

As described in the foregoing, leptospirosis diagnosis is conventionally conducted by MAT (microscopic agglutination test) in which a positive result is defined as a four-fold or greater rise in titer between two or more specimens taken at intervals of one week or by a method in which *leptospira* is isolated and cultured from a blood within one week, a cerebrospinal fluid 4-10 days, and a urine 10 days after the onset of the symptom. However, it takes several weeks to obtain results from the culturing methods. Early diagnosis is challenging due to the problem of requiring a long time for diagnosis.

In addition, leptospirosis must be diagnosed separately from other diseases such as hemorrhagic fever with renal symptoms, Tsutsugamushi disease, meningitis, encephalitis, hepatitis, etc.

In this regard, the present disclosure provides a novel method for diagnosis of leptospirosis, which allows early diagnosis of leptospirosis conveniently and quickly with high sensitivity and specificity and separately from other diseases and which is thus more accurate than conventional methods.

In an embodiment of the present disclosure, among multicopy genes, insertion sequence (IS) 1500 gene whose eight or more copies are found in *Leptospira interrogans*, one of bacteria causative of leptospirosis infection, was selected and primers and probes were designed to consist of various nucleotide sequences that were predicted to bind specifically to IS (insertion sequence) 1500 gene. The primers and probes extremely selective and specific for the IS (insertion sequence) 1500 of *leptospira* were chosen among a large number of primers and probes with diverse nucleotide sequences. The primers were named IS1500-290F primer (5-GATTGCCACAACAGATTC-3; SEQ ID NO: 1) and IS1500-475R primer (5-AATCGACCAACCCACTAC-3; SEQ ID NO: 2), and the probe was named IS1500-anti-312P probe (5-AGTTCGGAGCAACCCGATTCCCA-3; SEQ ID NO: 3).

According to experiments of the present disclosure, many primers and probes designed on the basis of the IS (insertion sequence) 1500 gene sequence failed to accurately amplify the gene, but it was found that the IS (insertion sequence) 1500 gene of *leptospira* can be detected at high sensitivity with only the primers of SEQ ID NOS: 1 and 2 and the probe of SEQ ID NO: 3.

Therefore, the present disclosure provides a composition for detecting a *leptospira* bacterium, the comprising a pair of the primers of SEQ ID NOS: 1 and 2 and the probe of SEQ ID NO: 3.

In the present disclosure, the primers and the probe can bind specifically to a gene of *leptospira* bacteria, preferably to an IS (insertion sequence) 1500 gene of *L. interrogans*, and the IS (insertion sequence) 1500 gene includes the nucleotide sequence of SEQ ID NO: 22.

Moreover, in another embodiment of the present disclosure, comparison of detection ability by PCR indicated that the primers and the probe of the present disclosure detected *leptospira* bacteria at higher sensitivity and specificity than conventional primers.

In an embodiment of the present disclosure, comparison of detection sensitivity and specificity was made between the conventional genes Hap1 and 16s rRNA known as target genes for detection of *leptospira* and the novel detection target gene IS (insertion sequence) 1500 discovered in the present disclosure. As a result, the method of the present disclosure exhibited a specificity of 100% and a sensitivity of 92.3% while sensitivity was measured to 9.1% for the target gene Hap1 and 0% for the target gene 16s rRNA.

From the data obtained, it was understood that *leptospira* can be detected at much higher specificity and sensitivity, compared to conventional methods, by real-time PCR using the primers and the probe discovered in the present disclosure, with the multicopy gene IS (insertion sequence) 1500 of the present disclosure serving as a target gene.

The amplicon of the real-time PCR using the primers of SEQ ID NOS: 1 and 2 and the probe of SEQ ID NO: 3 according to the present disclosure is an IS (insertion sequence) 1500 gene fragment including the 186-bp long nucleotide sequence of SEQ ID NO: 23.

Including the primers and the probe of the present disclosure which can detect the IS (insertion sequence) 1500 gene of *leptospira* at high sensitivity and accuracy, the composition for detection of a *leptospira* bacterium according to the present disclosure can be used to analyze whether a *leptospira* bacterium exist in a sample and thus as a composition for diagnosis of leptospirosis as well.

Therefore, the present disclosure provides a composition for diagnosis of leptospirosis, the composition comprising: a pair of primers of SEQ ID NOS: 1 and 2; and a probe of SEQ ID NO: 3.

The detecting or diagnostic composition of the present disclosure may comprise ingredients useful for a polymerase chain reaction (PCR), for example, a reaction buffer, dNTP, $Mg^{2+}$ ion, and a DNA polymerase, in addition to the primer pair and the probe according to the present disclosure.

The reaction buffer may contain 1-10 mM TrisHCl or 10-40 mM KCl (pH9.0) and the dNTP may be at least one selected from dATP, dTTP, dGTP, and dCTP.

In addition, the composition may comprise a stabilizer and/or a non-reactive dye for the convenience of experiment, stabilization, and reactivity improvement.

The non-reactive dye should be selected from among substances that do not influence polymerase chain reactions, and it is used to analyze or identify PCR products. Examples of substances that satisfy such conditions include water soluble dye such as rhodamine, tamra, lax, bromophenol blue, xylene cyanol, bromocresol red, and cresol red.

The composition may be provided in a liquid phase and preferably in a dry form in order to increase the stability, the convenience of storage and the long-term storage stability thereof. The drying may be performed using a known drying method, such as room temperature drying, drying at elevated temperature, freeze drying, or vacuum drying. Any drying method may be used as long as the composition does not lose its components. Depending on the type and amount of enzymes utilized, several drying processes may be used. After being prepared by mixing the components in a single tube and freezing or drying the same, the composition may be used in such a stable form, so that there are no needs of additional mixing processes during PCR, thereby preventing an error caused by mixing during reactions and improving the stability, reactivity, and preservation.

Except for the primer pair and the probe, the other components including a reaction buffer, dNTP, $Mg^{2+}$ ions, and DNA polymerases contained in the composition may be commercially available.

In addition, the present disclosure provides a kit for diagnosis of leptospirosis, comprising the composition.

The diagnostic kit according to the present disclosure comprises a pair of the primers of SEQ ID NOS: 1 and 2 and the probe of SEQ ID NO: 3 and as such, can quickly diagnose leptospirosis in an early stage with high accuracy.

The diagnosis may employ a polymerase chain reaction (PCR) to determine whether a specimen to be analyzed contains a *leptospira* bacterium or not. Examples of the PCR include conventional PCR, reverse transcription polymerase chain reaction (RT-PCR), and real-time polymerase chain reaction (real-time PCR). In an embodiment of the present disclosure, real-time PCR was conducted.

The diagnostic kit of the present disclosure may comprise a reverse transcriptase, a polymerase, complementary DNA (cDNA) as template DNA for PCR, and a reaction reagent such as a buffer, etc. in addition to the primer pair and the probe.

According to an embodiment of the present disclosure, the diagnostic kit of the present disclosure may be used in typical PCR or real-time PCR. In this regard, PCR may be conducted on a DNA genome of *leptospira* isolated from a specimen to be analyzed or on a complementary DNA (cDNA) as a template DNA which is separately obtained from an RNA gene of *leptospira* by reverse transcription using a reverse transcriptase.

The product of PCR may be separated by agarose gel electrophoresis, capillary electrophoresis, etc. Existence of a band corresponding to the length of the DNA amplified with the primer pair and the probe used may be diagnostic of leptospirosis.

Furthermore, the present disclosure employs the probe of SEQ ID NO: 3 which can bind specifically to the IS (insertion sequence) 1500 gene of *leptospira*, and the probe may be labeled with a fluorescent dye and a quencher at its respective ends. In detail, the probe may be labeled with a fluorescent dye at the 5' end thereof and with a quencher at the 3' end thereof. For example, a fluorescent dye emitting a specific wavelength such as red, green, blue, etc. is attached to the 5' end of the probe while a black hole quencher (BHQ) is linked to the 3' end of the probe. With the fluorescent dye and the quencher tethered to the probe, no fluorescent signals are detected because the quencher absorbs the light emitted by the fluorescent dye. In contrast, when the breakdown of the probe by the exonuclease activity of DNA polymerase breaks the reporter-quencher proximity during DNA synthesis and extension and thus allows unquenched emission of fluorescence, which can be detected. An increase in the product targeted by the probe at each PCR cycle therefore causes a proportional increase in fluorescence due to the breakdown of the probe and release of the fluorescent dye, which allows the detection of the fluorescent signal in real time and thus can determine the presence or absence of the viral gene on the basis of the fluorescent signal data acquired. This probe can be effectively used for real-time PCR.

Moreover, the present disclosure provides a method for diagnosis of leptospirosis infection and a method for providing information for diagnosis of leptospirosis.

Preferably, the method for providing information for diagnosis of leptospirosis comprises the steps of: (1) isolating a nucleic acid from a specimen separated from a subject suspected of leptospirosis; (2) conducting PCR amplification with the diagnostic kit of the present disclosure, with the isolated nucleic acid serving as a template; and (3) identifying a *L. interrogans* IS 1500 gene through step (2).

In addition, when the nucleic acid isolated from a specimen is RNA, RNA is reverse transcribed to synthesize cDNA which serves as a template on which real-time PCR amplification is carried out with the diagnostic kit of the present disclosure.

Examples of the specimen include, but are not limited to, blood, tissues, cells, sera, plasma, saliva, sputa, and urine from mammals.

In addition, the identification of the *leptospira* IS 1500 gene in the method may be carried out using at least one selected from the group consisting of capillary electrophoresis, DNA chip, gel electrophoresis, radioactivity measurement, fluorescence measurement, and phosphorescence measurement.

In addition, as used herein, the term "leptospirosis" refers to a disease caused as a result of the infection of *leptospira* bacteria.

As stated in the foregoing, the use of the pair of primers of SEQ ID NOS: 1 and 2 and the probe of SEQ ID NO: 3 that are all designed in the present disclosure to bind specifically to the IS 1500 gene of *leptospira* is advantageous in that *leptospira* bacteria can be quickly detected at high sensitivity and accuracy. When used on specimens from patients with leptospirosis and rats infected with *Leptospira*, real-time PCR analysis using the primers and probe of the present disclosure was successful in diagnosing the disease with a sensitivity of 90% or greater, a specificity of 100%, and in a short amount of time with high accuracy, as shown in the Examples below. Therefore, the method for diagnosis of leptospirosis and the method for providing information for diagnosis of leptospirosis, both using the composition, designed in the present disclosure, for detecting a *leptospira* bacterium, can quickly and accurately diagnose leptospirosis in an early phase, and can detect a *leptospira* bacterium in real time, thus monitoring the improvement of symptoms according to drug administration. Furthermore, the methods can discriminate leptospirosis from other diseases at high specificity, thereby finding advantageous applications in selecting more accurate therapies.

A better understanding of the present disclosure may be obtained through the following Examples which are set forth to illustrate, but are not to be construed as limiting the present disclosure.

Example 1

Selection of Target Gene and Construction of Primers and Probe for Detection of *Leptospira*

In order to discover a novel target gene for diagnosis of leptospirosis, which can improve sensitivity and accuracy of diagnosis compared to the conventional well-known target genes rpoB, hap1, and 16S rRNA, investigation was made into multicopy genes present specifically in *Leptospira*, rather than the single copy genes. In this regard, genes which exist in multicopies in *L. interrogans* were analyzed.

While multicopy genes in *L. interrogans* were screened, it was found that an insertion sequence (IS) gene exists in at least 8 copies according to *L. interrogans* strains. Sequence analysis targeting the IS1500 genes of *L. interrogans* was conducted to detect conserved regions. IS1500 gene sequence information for strains of *L. interrogans* are summarized in Table 1, below.

TABLE 1

IS1500 Sequence Information of *L. interrogans*

| GenBank Accession no. | sp. | Serovar | Strain |
|---|---|---|---|
| CP011410 | *L. interrogans* | Bratislava | PigK151 |
| KF648557 | *L. interrogans* | Canicola | Gui44 |
| AE016823 | *L. interrogans* | Copenhageni | Fiocruz L1-130 |

TABLE 1-continued

IS1500 Sequence Information of *L. interrogans*

| GenBank Accession no. | sp. | Serovar | Strain |
|---|---|---|---|
| CP012603 | *L. interrogans* | Hardjo | Norma |
| CP013147 | *L. interrogans* | Hardjo-prajitno | Hardjo-prajitno |
| U13012 | *L. interrogans* | icterohaemorrhagiae | |
| AE010300 | *L. interrogans* | Lai | 56601 |
| AE010301 | *L. interrogans* | Lai | 56601 |
| CP001221 | *L. interrogans* | Lai | IPAV |
| CP001222 | *L. interrogans* | Lai | IPAV |
| KJ586855 | *L. interrogans* | Lai | 56601 |
| CP006723 | *L. interrogans* | Linhai | 56609 |
| CP006724 | *L. interrogans* | Linhai | 56609 |
| CP006725 | *L. interrogans* | Linhai | 56609 |
| CP006726 | *L. interrogans* | Linhai | 56609 |
| CP011931 | *L. interrogans* | Manilae | UP-MMC-NIID LP |
| CP011933 | *L. interrogans* | Manilae | UP-MMC-NIID LP |
| CP011934 | *L. interrogans* | Manilae | UP-MMC-NIID HP |
| U13013 | *L. interrogans* | Pomona | |

In addition, numbers of copies of the insertion sequence (IS) gene that exist in various serotype *L. interrogans* strains are given in Table 2, below.

TABLE 2

Number of IS Gene Copy in Various Serotype *L. interrogans* Strains

| *L. interrogans* | IS1500 |
|---|---|
| Serovar Copenhageni | 8 copies |
| Serovar Lai | 7 copies |
| Strain RZ11 | 11 copies |
| Strain Verdun | at least 8 copies |

Analysis data for assemblies and alignments of IS 1500 genes present in various serotype *L. interrogans* strains are given in A and B of FIG. 1, respectively. Next, specific primers and probes targeting IS 1500 genes of *L. interrogans* were designed as shown in Table 3, below.

TABLE 3

Primers and Probes Designed to Detect Leptospira

| No. | Name | Sequence (5'->3') | Length | SEQ ID NO: | Product Size (bp) |
|---|---|---|---|---|---|
| 1 | IS1500-290F | GATTGCCACAACAGATTC | 18 | 1 | 186 |
| | IS1500-475R | AATCGACCAACCCACTAC | 18 | 2 | |
| | IS1500-anti-312P | AGTTCGGAGCAACCCGATTCCCA | 23 | 3 | |
| 2 | IS1500-QF | CTTGCTCCGTAAATTGAA | 18 | 4 | 171 |
| | IS1500-QR | GTCTCGTTCAGGATTCTA | 18 | 5 | |
| | IS1500-QP | CCGAAGCAACCGAACTAAGCC | 21 | 6 | |

TABLE 3-continued

Primers and Probes Designed to Detect Leptospira

| No. | Name | Sequence (5'->3') | Length | SEQ ID NO: | Product Size (bp) |
|---|---|---|---|---|---|
| 3 | lepto-IS1500_567F | CAAGGAAAACAGGAGAAA | 18 | 7 | 153 |
|  | lepto-IS1500_719R | CCCGAAAGAGRATCTTAA | 18 | 8 |  |
|  | lepto-IS1500_590P | TCGGATTGCCACAACAGATTCTAA | 24 | 9 |  |
| 4 | lepto-IS1500_567F | CAAGGAAAACAGGAGAAA | 18 | 10 | 181 |
|  | lepto-IS1500_747R | GATCCAGTATTACACAAAGA | 20 | 11 |  |
|  | lepto-IS1500_590P | TCGGATTGCCACAACAGATTCTAA | 24 | 12 |  |
| 5 | lepto-IS1500_567F | CAAGGAAAACAGGAGAAA | 18 | 13 | 192 |
|  | lepto-IS1500_758R | TCGAGAATAAAGATCCAG | 18 | 14 |  |
|  | lepto-IS1500_590P | TCGGATTGCCACAACAGATTCTAA | 24 | 15 |  |
| 6 | IS1500-55F | GTGTCTCGTTCAGGATTC | 18 | 16 | 176 |
|  | IS1500-230R | GTTCTTGCTCCGTAAATTG | 19 | 17 |  |
|  | IS1500-anti-192P | CCGAAGCAACCGAACTAAGCC | 21 | 18 |  |
| 7 | IS1500-459F | AGTGGGTTGGTCGATTTCAA | 20 | 19 | 99 |
|  | IS1500-557R | TGGATCCTCGATCCGAATGAA | 21 | 20 |  |
|  | IS1500-500P | TGTGCACCGCTCTTTCCAAAGCA | 23 | 21 |  |

Example 2

Selection of Optimal Primers and Probes for Detection of *Leptospira*

For sensitivity and specificity tests, real-time RT-PCR was performed using the primers and probes of Table 3 which were designed in Example 1 to detect IS 1500 target gene of *L. interrogans*.

Figure 2:
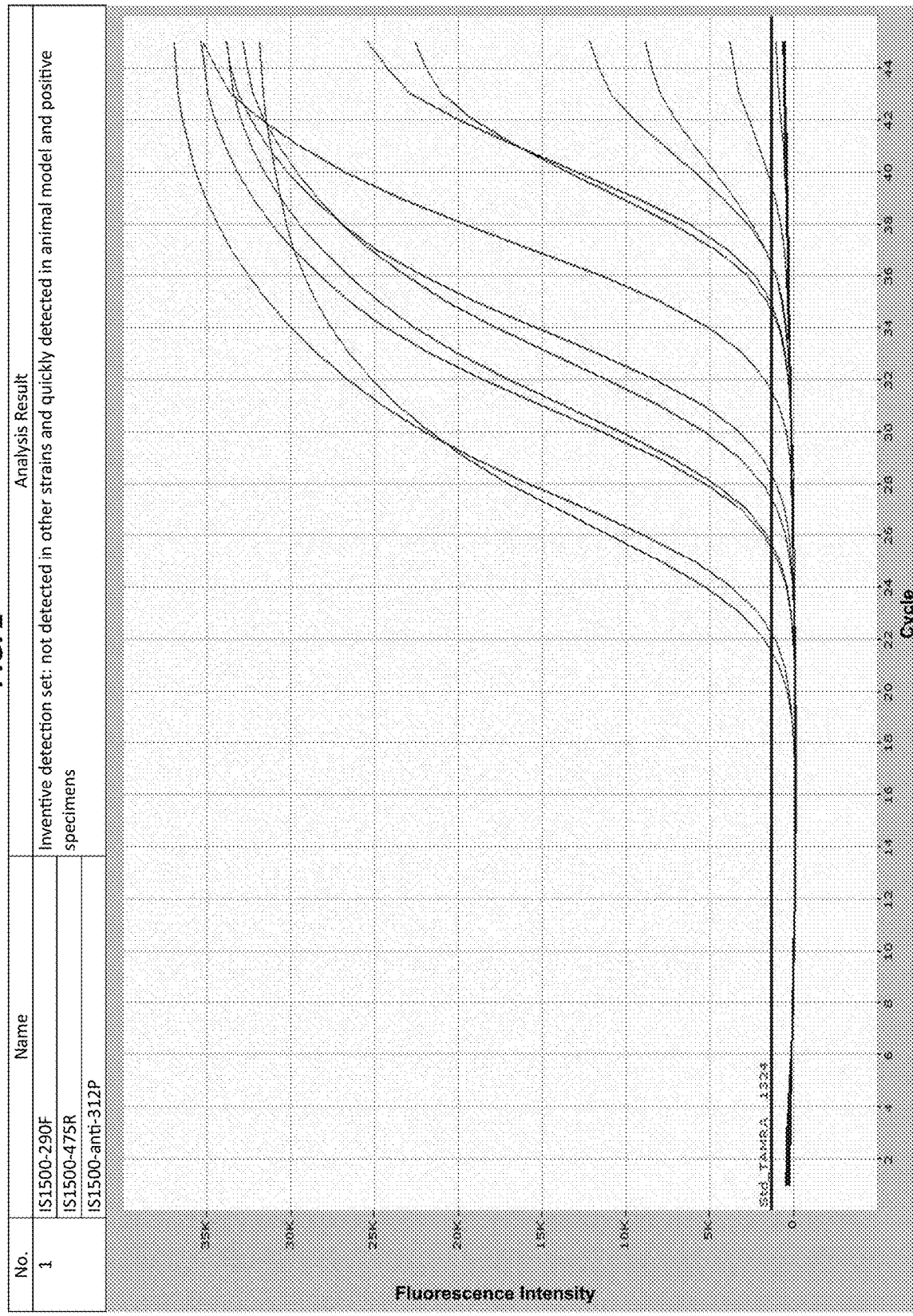
FIG. 2 shows results of an assay of various primer sets and proves for detection efficacy of *Leptospira* spp.
Figure 2:
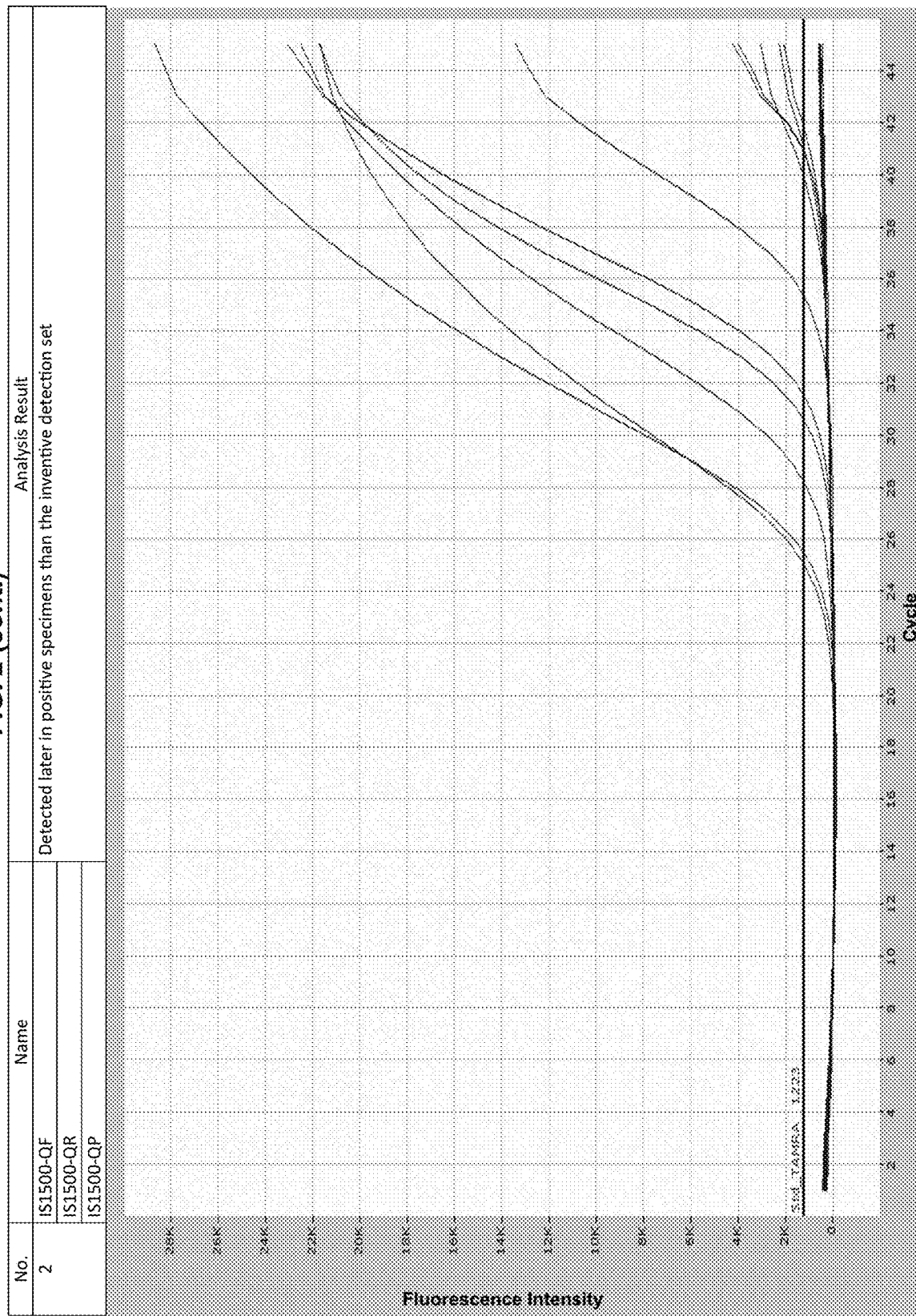
Figure 2:
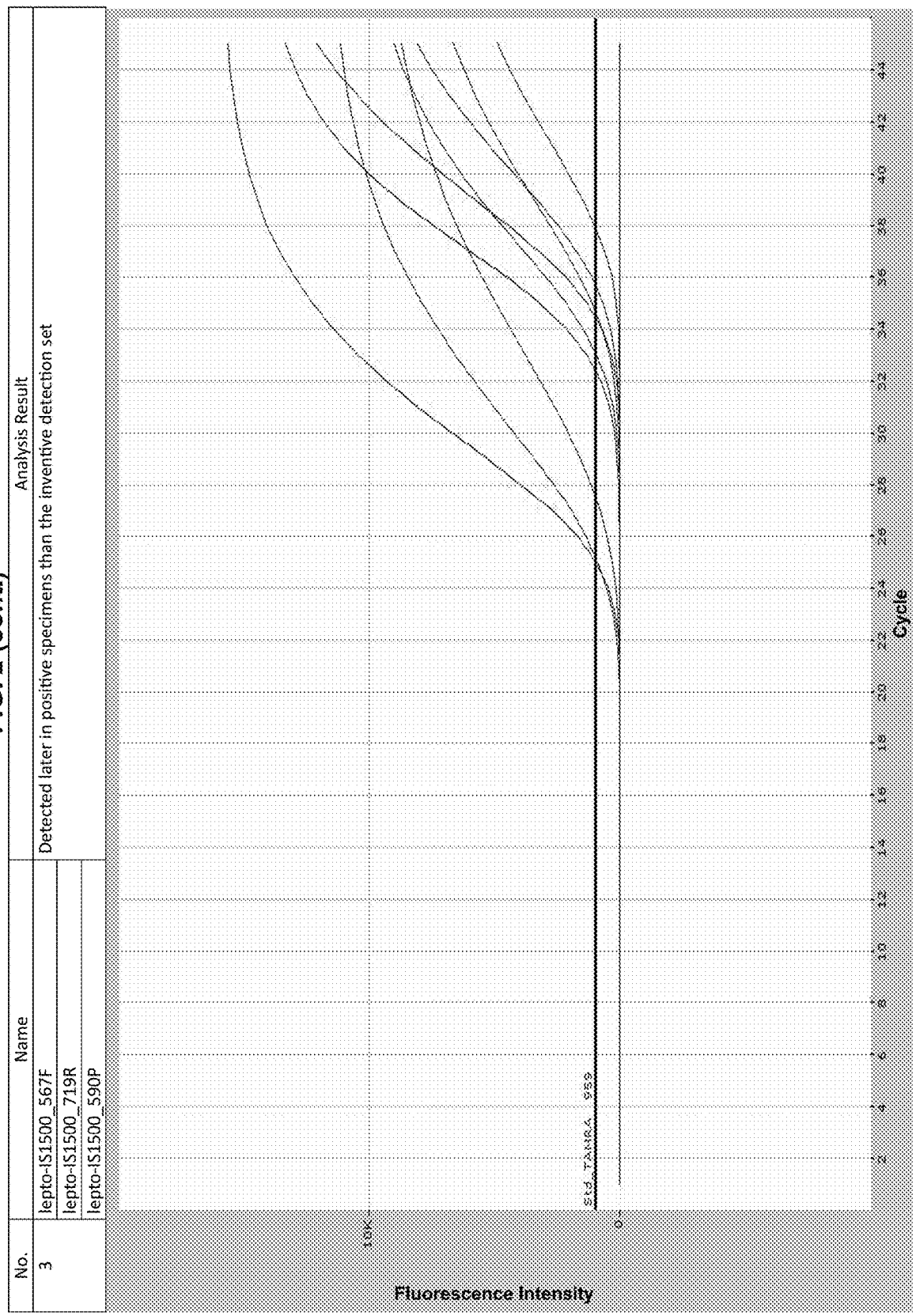
Figure 2:
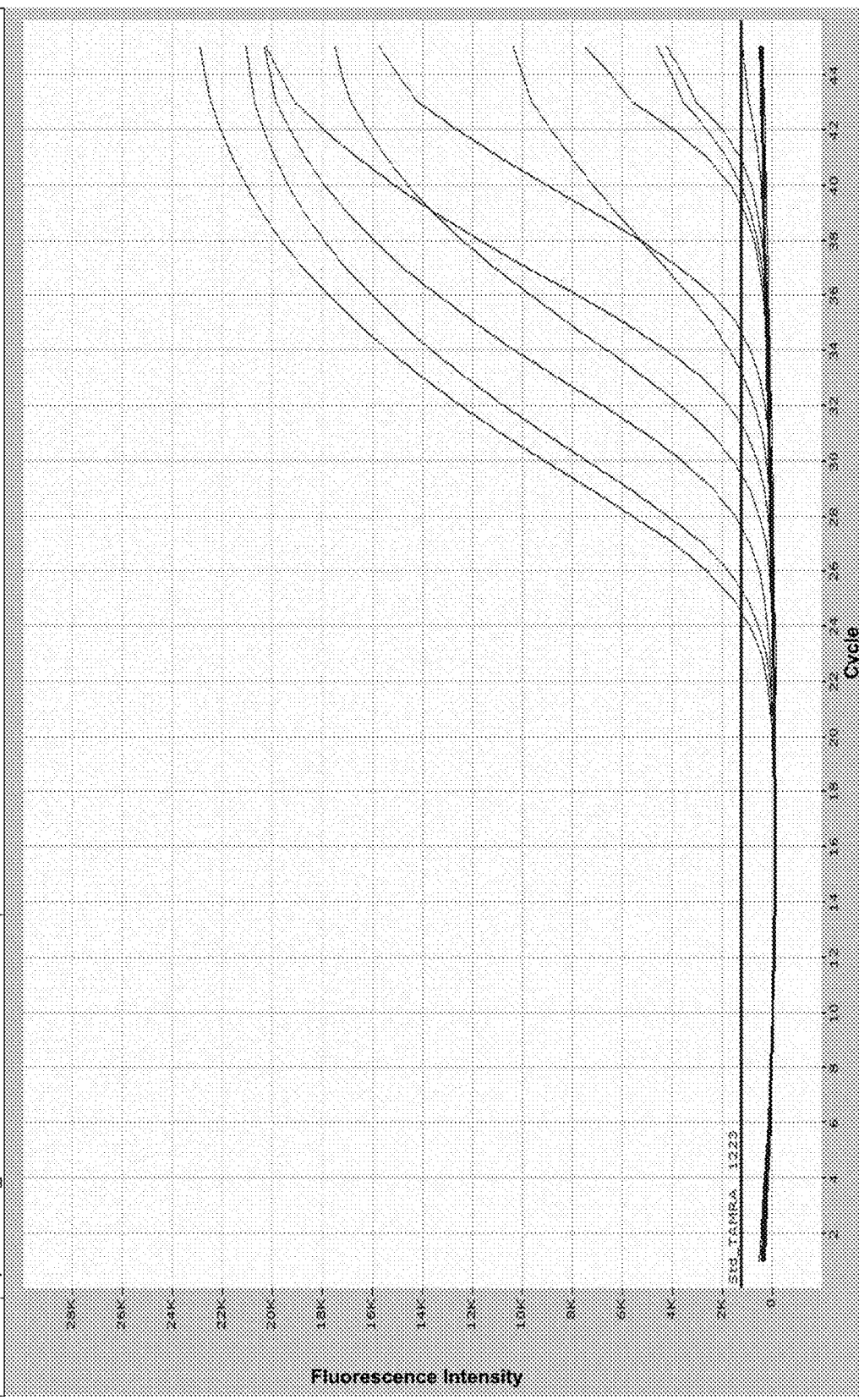
Figure 2:
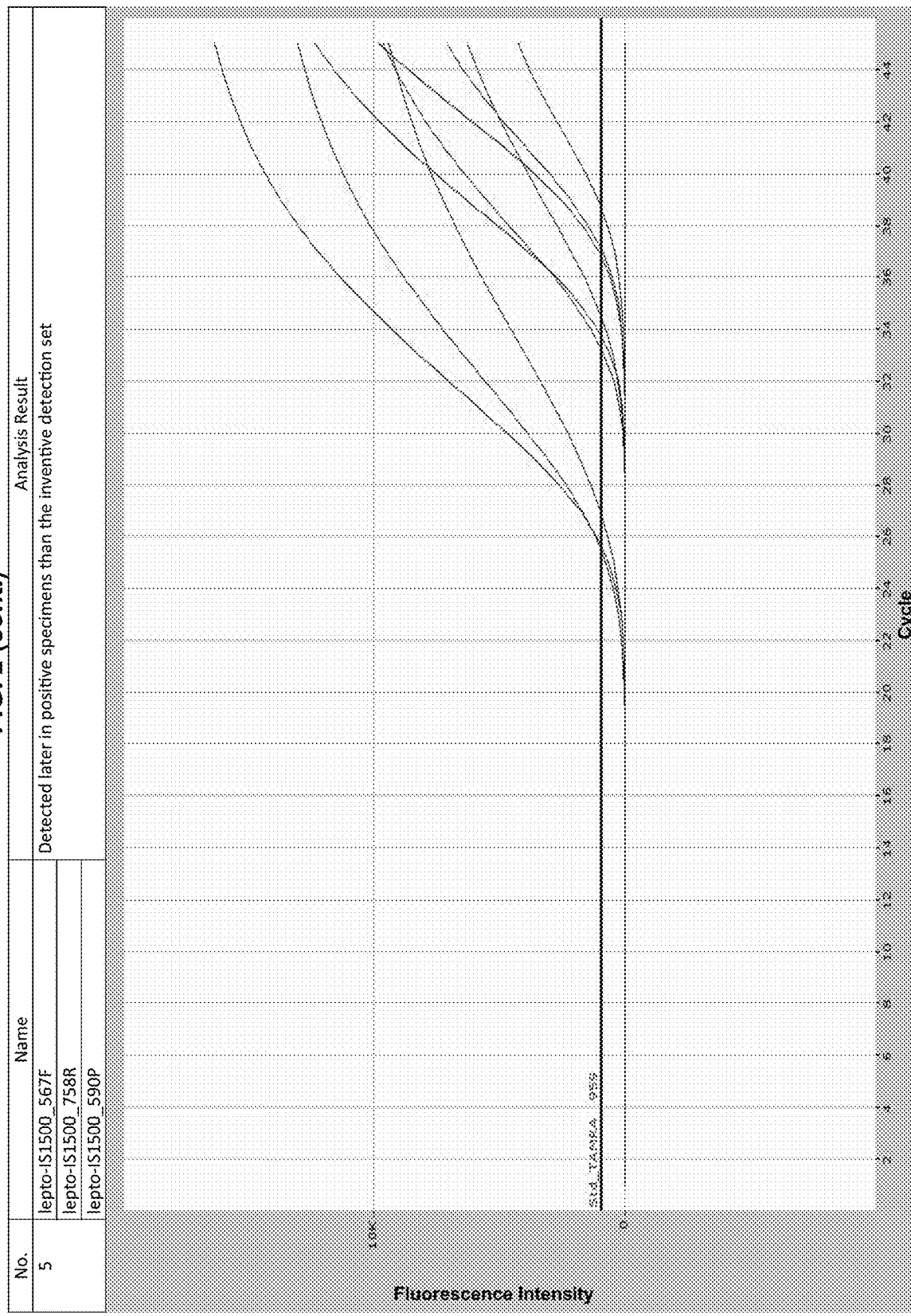
Figure 2:
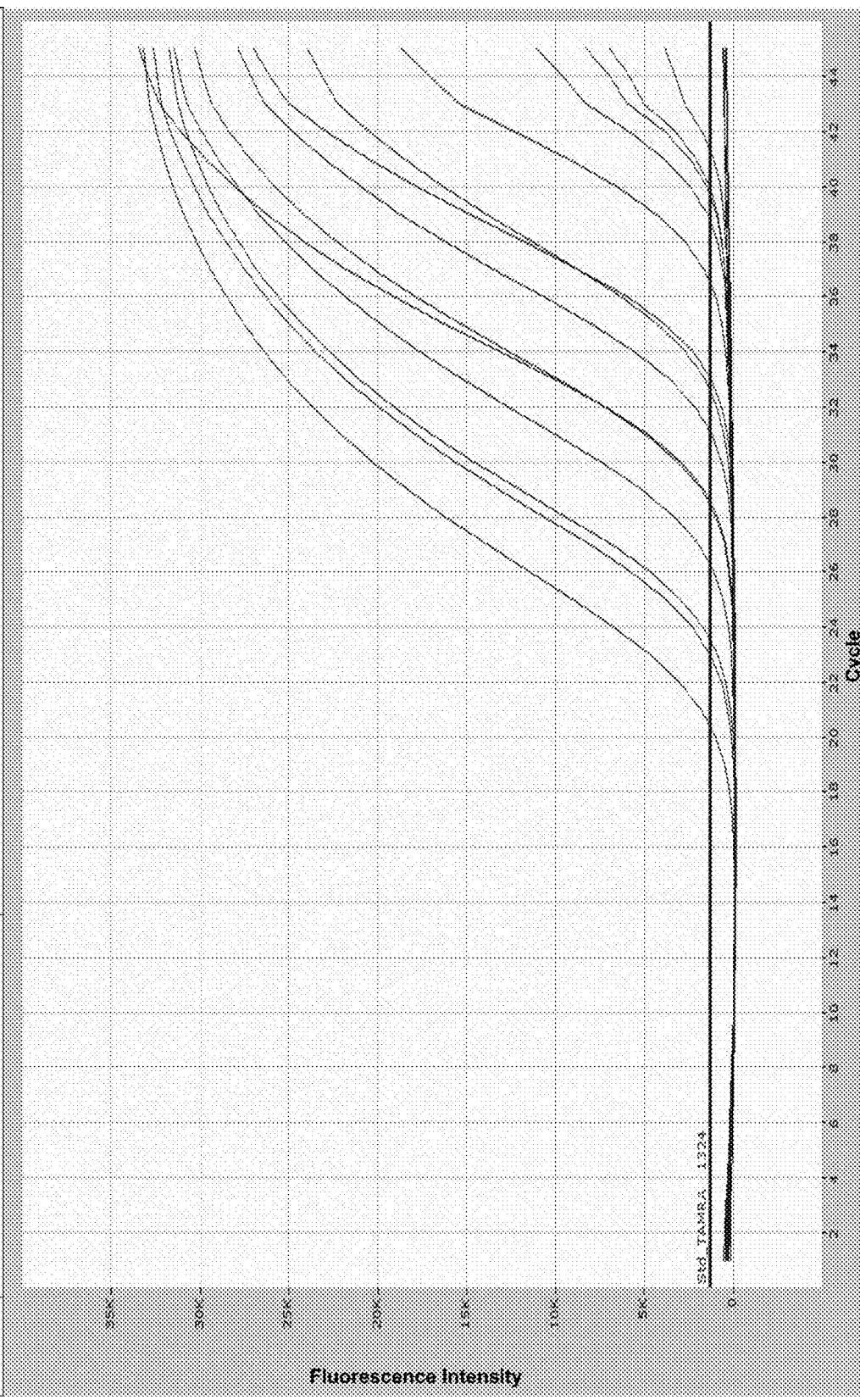

Among the primers and probes of Table 3, as shown in FIG. 2, the first (No. 1) primers (SEQ ID NOS: 1 and 2) and probe (SEQ ID NO: 3) exhibited higher sensitivity and specificity than the other primers and probes. Therefore, it is understood that the use of the first (No. 1) primers (SEQ ID NOS: 1 and 2) and probe (SEQ ID NO: 3) can reduce both time and cost and exhibit a greater detective effect, compared to conventional methods for detection and diagnosis of leptospirosis.

Example 3

Analysis of Primers and Probe for Sensitivity and Specificity for Detection of *Leptospira*

The primers and probe (SEQ ID NOS: 1 to 3 in Table 1) designed to detect or diagnose leptospirosis according to the present disclosure were analyzed for sensitivity and specificity for leptospirosis diagnosis in comparison with conventional primers and diagnostic methods.

To this end, experimental groups were classified according to detection methods as shown in Table 4, below. In Table 4, Lipl32 (hap1) C-PCR was performed as described in FEMS Microbiol Lett. 2005 Feb. 15; 243(2):437-45 (Polymerase Chain Reaction Assay Specific for Pathogenic *Leptospira* Based on the Gene hap1 Encoding the Hemolysis-Associated protein-1) and, for 16s C-PCR, reference was made to the method described in Clinical Samples. J Clin Microbiol. 1992 September; 30(9): 2219-2224. (Polymerase Chain Reaction for Detection of *Leptospira* spp.). The IS1500 real-time PCR using the primer set and probe of the present disclosure which targets the IS1500 gene started with thermal denaturation at 95° C. for 5 min, followed by 45 cycles of denaturation at 95° C. for 5 sec, annealing at 55° C. for 5 sec, and fluorescence intensity measurement. Then, the reaction was terminated at 25° C.

TABLE 4

| PCR | Target Gene | Primer or Probe |
|---|---|---|
| Lipl32 (hap1) C-PCR | Lipl32 (hemolysis-associated protein-1 (Hap1)) | Adia 217F primer (SEQ ID NO: 24) 5'-CCGTGATTTTCCTAACTA AGG-3' Adia 218R (SEQ ID NO: 25) 5'-CAGATTACTTAGTCGCGT CAGA-3' |
| 16s C-PCR | 16s rRNA | Lepto A (SEQ ID NO: 26) 5'-GGCGGCGCGTCTTAAACA TG-3' Lepto B (SEQ ID NO: 27) 5'-TTCCCCCCATTGAGCAAG ATT-3' |
| IS1500 real time PCR (Inventive) | IS1500 | IS1500-290F (SEQ ID NO: 1) IS1500-475R (SEQ ID NO: 2) IS1500-anti-312P (SEQ ID NO: 3) |

As specimens, bloods from rats which were infected with *Leptospira* interrogans and thus suffered from leptospirosis and from patients diagnosed with leptospirosis were taken.

These specimens were used for sensitivity assay.

For use as specimens for specificity assay, blood and renal tissues from rats infected with reference strains, *L. interrogans*, and other bacteria and tissues from SPF (specific pathogen-free) rats were employed. In addition, specimens from patients with other diseases were used for the assay.

Infected animal models used in the experiments are listed in Table 5, below.

TABLE 5

List of Infected Animal Models
L. interrogans injected Rat

| Serovar | Organ |
|---|---|
| Australis_R1 | Blood |
| Australis_R2 | Blood |
| hebdomadis_R1 | Blood |
| Icterohaemorrhagiae_R1 | Blood |
| Icterohaemorrhagiae_R2 | Blood |
| Canicola_R1 | Blood |
| Canicola_R2 | Blood |
| Lai_R1 | Blood |
| Lai_R2 | Blood |
| Ictero/Copenhageni_R1 | Blood |
| Ictero/Copenhageni_R2 | Blood |
| Hardjo_R1 | Blood |
| Hardjo_R2 | Blood |

<3-1> Assay for Sensitivity and Specificity for Detection of *Leptospira* Spp. in Animal Model Blood and renal tissues from each of the aforementioned *Leptospira* spp. and *L. interrogans* were assayed for sensitivity and specificity for detection of *Leptospira* spp. by the methods of Table 4.

TABLE 6

Specificity Assay in Animal Model

| Leptospira | | Infected Animal Model Result | | |
|---|---|---|---|---|
| | | Positive | Negative | Sum |
| Leptospira specific IS1500 Real-time PCR | Positive | 12 | 0 | 12 |
| | Negative | 1 | 18 | 19 |
| Total | | 13 | 18 | 31 |

TABLE 7

Sensitivity Assay in Animal Model

| Sensitivity Comparison | Lipl32(hap1) C-PCR | 16s rRNA C-PCR | IS1500 Real-time PCR |
|---|---|---|---|
| Positive No. | 1 | 0 | 12 |
| Total No. | 11 | 13 | 13 |
| Sensitivity (%) | 9.1% | 0% | 92.3% |

As shown in Tables 6 and 7, the real-time RT-PCR using the primers and probe of SEQ ID NOS: 1 to 3 which target the IS1500 gene discovered in the present disclosure was found to detect the bacteria with a specificity (diagnosis Ct cutoff value <38) of 92.3% (12/13) [95% CI: 62-99.5%] and a specificity of 100% (18/18) [95% CI: 78.1-100%].

This data indicates that the method of the present disclosure is higher in sensitivity than conventional PCR (9.1% (Lipl32), 0% (16s)).

<3-2> Sensitivity and Specificity Assay Using Specimen Isolated from Leptospirosis Patient In blood, urine, and sputum specimens from patients diagnosed with leptospirosis, the real-time PCR using the primers and probe of the present disclosure were assayed for sensitivity and specificity for leptospirosis diagnosis.

TABLE 8

Result of Real-Time PCR in Blood, Urine, and Sputum Specimens from Leptospirosis Patient

| Name | Date | Lab No. | Specimen | Ct value according to IS1500 Real-time PCR (inventive) |
|---|---|---|---|---|
| KANG Jung-O | 2019 Oct. 14 | 2019-697 | WB (whole blood) | 36.55 |
| KANG Jung-O | 2019 Oct. 16 | 2019-701 | WB | 35.31 |
| LEE Seung-O | 2018 Jul. 30 | 2018-780 | Plasma | 31.67 |
| HAN In-O | 2020 Jul. 27 | 2020-596 | WB | 34.7 |
| HAN In-O | 2020 Jul. 27 | 2020-596 | Sputum | 35.59 |
| LEE Sam-O | 2007 Aug. 10 | 2007-109 | Urine | 32.95 |
| PARK Jum-O | 2020 Aug. 25 | 2020-670 | WB | 31.22 |
| PARK Gui-O | 2020 Sep. 14 | 2020-704 | WB | 35.04 |
| LEE Myoung-O | 2020 Oct. 21 | 2020-971 | WB | 37.09 |
| LEE Myoung-O | 2020 Oct. 21 | 2020-971 | Urine | 31.11 | cf> UD: undetected

As can be seen in Table 8, the real-time PCR using the primers and probe designed in the present disclosure was found to detect the IS 1500 target gene of *L. interrogans* in the specimens from leptospirosis patients.

In addition, as a result of the application of the method of the present disclosure to the specimens obtained from patients diagnosed with other diseases, the IS 1500 target gene of *L. interrogans* was not detected in the specimens from the patients and healthy persons as shown in Table 9, below, indicating 100% specificity again.

TABLE 9

Data of Specificity Assay in Patients with Other Diseases and Persons in Health Examination

| 0 | Sample | Diagnosis | IS1500 Q PCR |
|---|---|---|---|
| 1 | 2016-201 | *Orientia tsutsugamushi* | Undetermined |
| 2 | 2016-202 | *O. tsutsugamushi* | Undetermined |
| 3 | 2016-211 | *O. tsutsugamushi* | Undetermined |
| 4 | 2016-214 | *O. tsutsugamushi* | Undetermined |
| 5 | 2016-216 | *O. tsutsugamushi* | Undetermined |
| 6 | 2016-228 | *O. tsutsugamushi* | Undetermined |
| 7 | 2016-355 | *O. tsutsugamushi* | Undetermined |
| 8 | 2017-1054 | *O. tsutsugamushi* | Undetermined |
| 9 | 2017-1057 | *O. tsutsugamushi* | Undetermined |
| 10 | 2017-1058 | *O. tsutsugamushi* | Undetermined |
| 11 | 2017-1062 | *O. tsutsugamushi* | Undetermined |
| 12 | 2017-651 | *Salmonella* gastroenteritis | Undetermined |
| 13 | 2017-1381 | Cholangitis | Undetermined |
| 14 | 2017-1383 | Pneumonia | Undetermined |
| 15 | 2017-1389 | Pneumonia | Undetermined |
| 16 | 2017-1355 | Pneumonia | Undetermined |
| 17 | 2017-1380 | Bronchitis | Undetermined |
| 18 | 2017-487 | Bacteremia | Undetermined |
| 19 | 2017-567 | Bacteremia | Undetermined |
| 20 | 2017-605 | Bacteremia | Undetermined |
| 21 | 2017-610 | Bacteremia | Undetermined |
| 22 | 2017-635 | Bacteremia | Undetermined |
| 23 | 2017-714 | Abscess | Undetermined |
| 24 | 2017-1386 | Bacteremia | Undetermined |
| 25 | 2017-600 | AIDS | Undetermined |
| 26 | 2017-683 | Syphilis | Undetermined |

TABLE 9-continued

Data of Specificity Assay in Patients with Other Diseases and Persons in Health Examination

| 0 | Sample | Diagnosis | IS1500 Q PCR |
|---|---|---|---|
| 27 | 2015-011 | Health Examination | Undetermined |
| 28 | 2015-012 | Health Examination | Undetermined |
| 29 | 2015-013 | Health Examination | Undetermined |
| 30 | 2015-014 | Health Examination | Undetermined |
| 31 | 2015-015 | Health Examination | Undetermined |
| 32 | 2015-016 | Health Examination | Undetermined |
| 33 | 2015-017 | Health Examination | Undetermined |

Taken together, the data obtained above demonstrate that real-time RT-PCR using the primers and probe designed in the present disclosure can detect and amplify the detection target IS 1500 gene of *L. interrogans*, a pathogen of leptospirosis, at high sensitivity and specificity, thereby quickly diagnosing leptospirosis with excellent accuracy and sensitivity, compared to conventional detection or diagnosis methods.

Although embodiments of the present disclosure have been described herein, it should be understood that the foregoing embodiments and advantages are merely examples and are not to be construed as limiting the present disclosure or the scope of the claims. Numerous other modifications and embodiments can be devised by those skilled in the art that will fall within the spirit and scope of the principles of this disclosure, and the present teaching can also be readily applied to other types of apparatuses. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A composition for diagnosis of a *Leptospira* bacterium, the composition comprising a pair of primers of SEQ ID NOS: 1 and 2 and a probe,
   wherein the probe comprises SEQ ID NO: 3 and first and second labels,
   wherein the first label comprises a fluorescent dye,
   wherein the *Leptospira* bacterium is *L. interrogans*, and
   wherein SEQ ID NOS:1-3 bind specifically to a *L. interrogans* IS 1500 gene including the nucleotide sequence of SEQ ID NO: 22.

2. A kit for diagnosis of leptospirosis, comprising the composition of claim 1.

3. A method for diagnosing leptospirosis, the method comprising:
   isolating a nucleic acid from a specimen separated from a subject suspected of leptospirosis;
   conducting PCR amplification with a diagnostic kit, with the isolated nucleic acid serving as a template;
   identifying a *L. interrogans* IS 1500 gene through the conducting; and
   obtaining a diagnosis for leptospirosis when the *L. interrogans* IS 1500 gene is identified,
   wherein the diagnostic kit comprises a pair of primers of SEQ ID NOS: 1 and 2, and a probe, and
   wherein the probe comprises SEQ ID NO:3 and first and second labels,
   wherein the *L. interrogans* IS 1500 gene includes the nucleotide sequence of SEQ ID NO: 22.

4. The method of claim 3, wherein the specimen is blood, a tissue, a cell, serum, plasma, saliva, sputum, or urine from a mammal.

5. The method of claim 3, wherein the PCR amplification is selected from the group consisting of conventional polymerase chain reaction (C-PCR), nested PCR (N-PCR), multiplex PCR, real-time PCR, quantitative real-time PCR, and reverse transcription PCR.

6. The method of claim 3, wherein the first label comprises a fluorescent dye.

7. The method of claim 6, wherein the second label comprises a quencher.

8. The composition of claim 1, wherein the second label comprises a quencher.

* * * * *

SEQUENCE LISTING

```
<160> NUMBER OF SEQ ID NOS: 27

<210> SEQ ID NO 1
<211> LENGTH: 18
<212> TYPE: DNA
<213> ORGANISM: Artificial Sequence
<220> FEATURE:
<223> OTHER INFORMATION: IS1500-290F primer

<400> SEQUENCE: 1
gattgccaca acagattc                                                 18

<210> SEQ ID NO 2
<211> LENGTH: 18
<212> TYPE: DNA
<213> ORGANISM: Artificial Sequence
<220> FEATURE:
<223> OTHER INFORMATION: IS1500-475R primer

<400> SEQUENCE: 2
aatcgaccaa cccactac                                                 18

<210> SEQ ID NO 3
<211> LENGTH: 23
<212> TYPE: DNA
<213> ORGANISM: Artificial Sequence
<220> FEATURE:
<223> OTHER INFORMATION: IS1500-anti-312P probe

<400> SEQUENCE: 3
agttcggagc aacccgattc cca                                           23

<210> SEQ ID NO 4
<211> LENGTH: 18
<212> TYPE: DNA
<213> ORGANISM: Artificial Sequence
<220> FEATURE:
<223> OTHER INFORMATION: IS1500-QF primer

<400> SEQUENCE: 4
cttgctccgt aaattgaa                                                 18

<210> SEQ ID NO 5
<211> LENGTH: 18
<212> TYPE: DNA
<213> ORGANISM: Artificial Sequence
```

```
<220> FEATURE:
<223> OTHER INFORMATION: IS1500-QR primer

<400> SEQUENCE: 5
gtctcgttca ggattcta                                              18

<210> SEQ ID NO 6
<211> LENGTH: 21
<212> TYPE: DNA
<213> ORGANISM: Artificial Sequence
<220> FEATURE:
<223> OTHER INFORMATION: IS1500-QP probe

<400> SEQUENCE: 6
ccgaagcaac cgaactaagc c                                          21

<210> SEQ ID NO 7
<211> LENGTH: 18
<212> TYPE: DNA
<213> ORGANISM: Artificial Sequence
<220> FEATURE:
<223> OTHER INFORMATION: lepto-IS1500_567F primer

<400> SEQUENCE: 7
caaggaaaac aggagaaa                                              18

<210> SEQ ID NO 8
<211> LENGTH: 18
<212> TYPE: DNA
<213> ORGANISM: Artificial Sequence
<220> FEATURE:
<223> OTHER INFORMATION: lepto-IS1500_719R primer

<400> SEQUENCE: 8
cccgaaagag ratcttaa                                              18

<210> SEQ ID NO 9
<211> LENGTH: 24
<212> TYPE: DNA
<213> ORGANISM: Artificial Sequence
<220> FEATURE:
<223> OTHER INFORMATION: lepto-IS1500_590P probe

<400> SEQUENCE: 9
tcggattgcc acaacagatt ctaa                                       24

<210> SEQ ID NO 10
<211> LENGTH: 18
<212> TYPE: DNA
<213> ORGANISM: Artificial Sequence
<220> FEATURE:
<223> OTHER INFORMATION: lepto-IS1500_567F primer

<400> SEQUENCE: 10
caaggaaaac aggagaaa                                              18

<210> SEQ ID NO 11
<211> LENGTH: 20
<212> TYPE: DNA
<213> ORGANISM: Artificial Sequence
<220> FEATURE:
<223> OTHER INFORMATION: lepto-IS1500_747R primer

<400> SEQUENCE: 11
gatccagtat tacacaaaga                                            20
```

```
<210> SEQ ID NO 12
<211> LENGTH: 24
<212> TYPE: DNA
<213> ORGANISM: Artificial Sequence
<220> FEATURE:
<223> OTHER INFORMATION: lepto-IS1500_590P probe

<400> SEQUENCE: 12
tcggattgcc acaacagatt ctaa                                            24

<210> SEQ ID NO 13
<211> LENGTH: 18
<212> TYPE: DNA
<213> ORGANISM: Artificial Sequence
<220> FEATURE:
<223> OTHER INFORMATION: lepto-IS1500_567F primer

<400> SEQUENCE: 13
caaggaaaac aggagaaa                                                   18

<210> SEQ ID NO 14
<211> LENGTH: 18
<212> TYPE: DNA
<213> ORGANISM: Artificial Sequence
<220> FEATURE:
<223> OTHER INFORMATION: lepto-IS1500_758R primer

<400> SEQUENCE: 14
tcgagaataa agatccag                                                   18

<210> SEQ ID NO 15
<211> LENGTH: 24
<212> TYPE: DNA
<213> ORGANISM: Artificial Sequence
<220> FEATURE:
<223> OTHER INFORMATION: lepto-IS1500_590P probe

<400> SEQUENCE: 15
tcggattgcc acaacagatt ctaa                                            24

<210> SEQ ID NO 16
<211> LENGTH: 18
<212> TYPE: DNA
<213> ORGANISM: Artificial Sequence
<220> FEATURE:
<223> OTHER INFORMATION: IS1500-55F primer

<400> SEQUENCE: 16
gtgtctcgtt caggattc                                                   18

<210> SEQ ID NO 17
<211> LENGTH: 19
<212> TYPE: DNA
<213> ORGANISM: Artificial Sequence
<220> FEATURE:
<223> OTHER INFORMATION: IS1500-230R primer

<400> SEQUENCE: 17
gttcttgctc cgtaaattg                                                  19

<210> SEQ ID NO 18
<211> LENGTH: 21
<212> TYPE: DNA
<213> ORGANISM: Artificial Sequence
<220> FEATURE:
<223> OTHER INFORMATION: IS1500-anti-192P probe
```

<400> SEQUENCE: 18
ccgaagcaac cgaactaagc c                                          21

<210> SEQ ID NO 19
<211> LENGTH: 20
<212> TYPE: DNA
<213> ORGANISM: Artificial Sequence
<220> FEATURE:
<223> OTHER INFORMATION: IS1500-459F primer

<400> SEQUENCE: 19
agtgggttgg tcgatttcaa                                            20

<210> SEQ ID NO 20
<211> LENGTH: 21
<212> TYPE: DNA
<213> ORGANISM: Artificial Sequence
<220> FEATURE:
<223> OTHER INFORMATION: IS1500-557R primer

<400> SEQUENCE: 20
tggatcctcg atccgaatga a                                          21

<210> SEQ ID NO 21
<211> LENGTH: 23
<212> TYPE: DNA
<213> ORGANISM: Artificial Sequence
<220> FEATURE:
<223> OTHER INFORMATION: IS1500-500P probe

<400> SEQUENCE: 21
tgtgcaccgc tctttccaaa gca                                        23

<210> SEQ ID NO 22
<211> LENGTH: 843
<212> TYPE: DNA
<213> ORGANISM: Artificial Sequence
<220> FEATURE:
<223> OTHER INFORMATION: L. interrogans IS 1500 gene sequence

<400> SEQUENCE: 22
atggaaactc atcgatttga gtattcgatt caaagcatgg ctaacgtttt aggagtgtct    60
cgttcaggat tctatcaatt tctaaaacgg agtaaaaacg aattagaaaa atataatcct   120
gaacttgtcg agttcattcg ggaaacgtgg ctaacaagcc gtaagaatta cggcttagtt   180
cggttgcttc gggaagtgaa gaaagtgtat tcaatttacg gagcaagaac ggttcgaaaa   240
gtgatgaaac tttgtgaaat tcaaggaaaa caggagaaac gttttcggat tgccacaaca   300
gattctaatc atgggaatcg ggttgctccg aacttagttc aacggaattt caaaccgaat   360
cagaagaatc ggatctgggt ttcagatatt acttttttaa gatcctcttt cgggtggatt   420
tatctttgtg taatactgga tctttattct cgaaaagtag tgggttggtc gatttcaaat   480
tctaatgatt ctaagttagt gtgcaccgct ctttccaaag caatcgaatg tagaaatcct   540
cctaagggtt tagttttttca ttcggatcga ggatccaatt attgttcgta cgaaactcga   600
aggtatctgt taaataataa actaagaagg agtaatagta gaaagggaaa ttgttgggac   660
aacgcagtcg ctgagtcctt ctttggttct ctgaaaagag aaatggaata taattacttt   720
tataaaattc aagaagccga agaattactt tttgatcata tagaggttta ttataataga   780
cacagatctc attcgtcatt agactttgtg agtcctgtgc aatttgaagt aaatgctgcg   840

| | |
|---|---|
| taa | 843 |

<210> SEQ ID NO 23
<211> LENGTH: 187
<212> TYPE: DNA
<213> ORGANISM: Artificial Sequence
<220> FEATURE:
<223> OTHER INFORMATION: PCR product

<400> SEQUENCE: 23

| | |
|---|---|
| gattgccaca acagattcta atcatgggaa tcgggttgct ccgaacttag ttcaacggaa | 60 |
| tttcaaaccg aatcagaaga atcggatctg ggtttcagat attactttt taagatcctc | 120 |
| tttcgggtgg atttatcttt gtgtaatact ggatctttat tctcgaaaag tagtgggttg | 180 |
| gtcgatt | 187 |

<210> SEQ ID NO 24
<211> LENGTH: 21
<212> TYPE: DNA
<213> ORGANISM: Artificial Sequence
<220> FEATURE:
<223> OTHER INFORMATION: Adia 217F primer

<400> SEQUENCE: 24

| | |
|---|---|
| ccgtgatttt cctaactaag g | 21 |

<210> SEQ ID NO 25
<211> LENGTH: 22
<212> TYPE: DNA
<213> ORGANISM: Artificial Sequence
<220> FEATURE:
<223> OTHER INFORMATION: Adia 218R primer

<400> SEQUENCE: 25

| | |
|---|---|
| cagattactt agtcgcgtca ga | 22 |

<210> SEQ ID NO 26
<211> LENGTH: 20
<212> TYPE: DNA
<213> ORGANISM: Artificial Sequence
<220> FEATURE:
<223> OTHER INFORMATION: Lepto A primer

<400> SEQUENCE: 26

| | |
|---|---|
| ggcggcgcgt cttaaacatg | 20 |

<210> SEQ ID NO 27
<211> LENGTH: 21
<212> TYPE: DNA
<213> ORGANISM: Artificial Sequence
<220> FEATURE:
<223> OTHER INFORMATION: Lepto B primer

<400> SEQUENCE: 27

| | |
|---|---|
| ttcccccat tgagcaagat t | 21 |